(12) United States Patent
Pan et al.

(10) Patent No.: US 9,181,238 B2
(45) Date of Patent: Nov. 10, 2015

(54) N-(PYRIDIN-2-YL)SULFONAMIDES AND COMPOSITIONS THEREOF AS PROTEIN KINASE INHIBITORS

(75) Inventors: Shifeng Pan, San Diego, CA (US); John E. Tellew, La Jolla, CA (US); Yongqin Wan, Irvine, CA (US); Yongping Xie, San Diego, CA (US); Xing Wang, San Diego, CA (US); Xia Wang, San Diego, CA (US); Shenlin Huang, San Diego, CA (US); Zuosheng Liu, San Diego, CA (US); Qiong Zhang, El Cerrito, CA (US)

(73) Assignee: NOVARTIS AG, Basel (CH)

( * ) Notice: Subject to any disclaimer, the term of this patent is extended or adjusted under 35 U.S.C. 154(b) by 527 days.

(21) Appl. No.: 13/577,209

(22) PCT Filed: Feb. 4, 2011

(86) PCT No.: PCT/US2011/023812
§ 371 (c)(1),
(2), (4) Date: Sep. 28, 2012

(87) PCT Pub. No.: WO2011/097526
PCT Pub. Date: Aug. 11, 2011

(65) Prior Publication Data
US 2013/0143899 A1 Jun. 6, 2013

Related U.S. Application Data

(60) Provisional application No. 61/301,801, filed on Feb. 5, 2010.

(51) Int. Cl.
| | |
|---|---|
| *A61K 31/444* | (2006.01) |
| *C07D 213/75* | (2006.01) |
| *C07D 471/04* | (2006.01) |
| *C07D 401/14* | (2006.01) |
| *A61K 31/506* | (2006.01) |
| *A61K 31/519* | (2006.01) |
| *A61K 45/06* | (2006.01) |

(52) U.S. Cl.
CPC ............ *C07D 471/04* (2013.01); *A61K 31/444* (2013.01); *A61K 31/506* (2013.01); *A61K 31/519* (2013.01); *A61K 45/06* (2013.01); *C07D 401/14* (2013.01)

(58) Field of Classification Search
CPC ............................ A61K 31/444; C07D 213/75
USPC ........... 514/352; 544/333, 405; 546/118, 122, 546/304
See application file for complete search history.

(56) References Cited

U.S. PATENT DOCUMENTS

2002/0137774 A1    9/2002    Riedl et al.

FOREIGN PATENT DOCUMENTS

| WO | 2005034869 | | 4/2005 |
| WO | 2007067444 | | 6/2007 |
| WO | 2008051757 | | 5/2008 |
| WO | WO 2011/097526 | * | 8/2011 |

OTHER PUBLICATIONS

Jordan, V. C. Nature Reviews: Drug Discovery, 2, 2003, 205.*
Hackam, et al. JAMA, 296(14), 2006, 1731-1732.*
Philip Wickens, et al., SAR of a novel 'Anthranilamide Like' series of VEGFR-2, multi protein kinase inhibitors for the treatment of cancer, Bioorganic & Medicinal Chemistry Letters, 2007, vol. 17, No. 15, 4378-4381.

* cited by examiner

*Primary Examiner* — Douglas M Willis
(74) *Attorney, Agent, or Firm* — Daniel E. Raymond; Genomics Institute of the Novartis Research Foundation

(57) ABSTRACT

The invention provides a novel class of compounds of Formula (I) (wherein A, Y, $R_2$, $R_3$, $R_4$ and $R_5$ are defined in the summary of the invention), pharmaceutical compositions comprising such compounds and methods of using such compounds to treat or prevent diseases or disorders associated with abnormal or deregulated kinase activity, particularly diseases or disorders that involve abnormal activation of B-Raf.

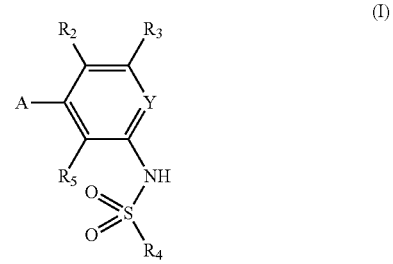

11 Claims, No Drawings

N-(PYRIDIN-2-YL)SULFONAMIDES AND COMPOSITIONS THEREOF AS PROTEIN KINASE INHIBITORS

CROSS-REFERENCE TO RELATED APPLICATIONS

This application is a 371 U.S. national phase application of international application number PCT/US2011/023812 filed 4 Feb. 2011, which application claims the benefit of priority under 35 U.S.C. §119(e) to U.S. Provisional Patent Application No. 61/301,810, filed 5 Feb., 2010. The disclosure of these applications are incorporated herein by reference in their entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of B-Raf.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, trkB, Met, and the fibroblast growth factor receptor, FGFR3; non-receptor tyrosine kinases such as Abl and the fusion kinase BCR-Abl, Lck, Csk, Fes, Bmx and c-src; and serine/threonine kinases such as B-Raf, sgk, MAP kinases (e.g., MKK4, MKK6, etc.) and SAPK2α, SAPK2β and SAPK3. Aberrant kinase activity has been observed in many disease states including benign and malignant proliferative disorders as well as diseases resulting from inappropriate activation of the immune and nervous systems.

The novel compounds of this invention inhibit the activity of B-Raf or mutant forms thereof (for example V600E) and are, therefore, expected to be useful in the treatment of B-Raf-associated diseases.

SUMMARY OF THE INVENTION

In one aspect, the present invention provides compounds of Formula I:

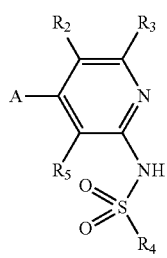

I in which A is selected from a and b:

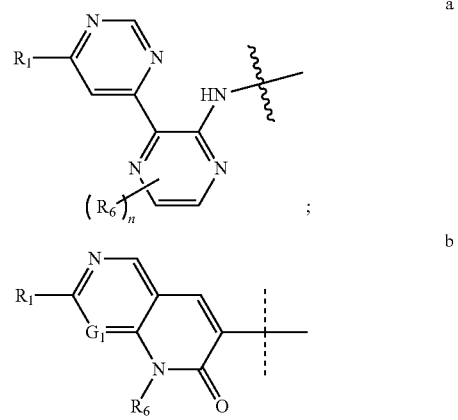

in which:

$G_1$ is selected from N or $CR_8$; $R_8$ is selected from hydrogen, halo, cyano and $C_{1-4}$alkyl optionally substituted by 1 to 3 groups independently selected from hydroxy, halo, cyano, oxo, $C_{1-4}$alkyl, halo-substituted-$C_{1-4}$alkyl, $C_{1-4}$alkoxy, halo-substituted-$C_{1-4}$alkoxy and $NHC(O)OR_9$; wherein $R_9$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

n is selected from 0, 1 and 2;

$R_1$ is selected from hydrogen, $C_{1-4}$alkyl and $-NHR_{20}$, wherein $R_{20}$ is selected from hydrogen and $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, $NHC(O)OR_{10}$ and $S(O)_{0-2}R_{10}$; wherein $R_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy; wherein any alkyl of $R_1$ is optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

$R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;

$R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;

$R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy;

$R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkoxy; and the N-oxide derivatives, prodrug derivatives, protected derivatives, the tautomers, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly B-Raf activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly B-Raf activity, particularly mutant B-raf (for example V600E), contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted-$C_{1-4}$alkyl means and alkyl group (branched or unbranched) wherein any of the hydrogens can be substituted with a halogen. For example, halo-substituted-$C_{1-4}$alkyl can be trifluoromethyl, difluoroethyl, pentafluoroethyl, and the like. Similarly, hydroxy-substituted-$C_{1-6}$alkyl means and alkyl group (branched or unbranched) wherein any of the hydrogens can be substituted with a hydroxyl. For example, hydroxy-substituted-$C_{1-6}$alkyl includes 2-hydroxyethyl, and the like. Similarly, cyano-substituted-$C_{1-6}$alkyl means and alkyl group (branched or unbranched) wherein any of the hydrogens can be substituted with cyano.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heteroaryl" is as defined for aryl above where one or more of the ring members is a heteroatom. For example, heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes 2H-pyran, 4H-pyran, piperidine, 1,4-dioxane, morpholine, 1,4-dithiane, thiomorpholino, imidazolidin-2-one, tetrahydrofuran, piperazine, 1,3,5-trithiane, pyrrolidine, pyrrolidinyl-2-one, piperidine, piperidinone, 1,4-dioxa-8-aza-spiro[4.5]dec-8-yl, etc.

"Halogen" (or halo) represents chloro, fluoro, bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of kinase related disease, particularly B-Raf kinase related diseases. For example, metastatic melanomas, solid tumors, brain tumors such as Glioblastoma multiform (GBM), acute myelogenous leukemia (AML), papillary thyroid carcinoma, ovarian low-grade carcinoma, and colorectal cancer.

In one embodiment, with reference to compounds of Formula I, are compounds of Formula Ia:

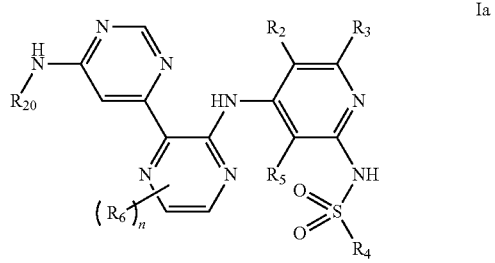

Ia in which:
n is selected from 0, 1 and 2;
$R_{20}$ is selected from hydrogen and $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, NHC(O)OR$_{10}$ and S(O)$_{0-2}$R$_{10}$; wherein R$_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;
$R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;
$R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;
$R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy; and
$R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkoxy.

In another embodiment, n is 0; $R_{20}$ is selected from methyl and ethyl; wherein said methyl and ethyl are optionally substituted by 1 to 3 groups independently selected from cyano, trifluoromethyl, methyl-sulfonyl, halo and methyl; $R_2$ is fluoro; $R_3$ is hydrogen; $R_4$ is selected from propyl; and $R_5$ is selected from fluoro and chloro.

In a further embodiment are compounds selected from: N-(4-(3-(6-(ethylamino)pyrimidin-4-yl)pyrazin-2-ylamino)-3,5-difluoropyridin-2-yl)propane-1-sulfonamide; N-(4-(3-(6-(2-cyanoethylamino)pyrimidin-4-yl)pyrazin-2-ylamino)-3,5-difluoropyridin-2-yl)propane-1-sulfonamide; N-(3,5-difluoro-4-(3-(6-(3,3,3-trifluoropropylamino)pyrimidin-4-yl)pyrazin-2-ylamino)pyridin-2-yl)propane-1-sulfonamide; N-(4-(3-(6-(2,2-difluoroethylamino)pyrimidin-4-yl)pyrazin-2-ylamino)-3,5-difluoropyridin-2-yl)propane-1-sulfonamide; N-(3,5-difluoro-4-(3-(6-(methylamino)pyrimidin-4-yl)pyrazin-2-ylamino)pyridin-2-yl)propane-1-sulfonamide; N-(3-chloro-4-(3-(6-(ethylamino)pyrimidin-4-yl)pyrazin-2-ylamino)-5-fluoropyridin-2-yl)propane-1-sulfonamide; N-(3,5-difluoro-4-(3-(6-(2,2,2-trifluoroethylamino)pyrimidin-4-yl)pyrazin-2-ylamino)pyridin-2-yl)propane-1-sulfonamide; N-(3,5-difluoro-4-(3-(6-(2-(methylsulfonyl)ethylamino)pyrimidin-4-yl)pyrazin-2-ylamino)pyridin-2-yl)propane-1-sulfonamide; N-(4-((3-(6-((2-cyanoethyl)amino)pyrimidin-4-yl)pyrazin-2-yl)amino)-3-fluoropyridin-2-yl)propane-1-sulfonamide and N-(4-(3-(6-(2-cyanopropylamino)pyrimidin-4-yl)pyrazin-2-ylamino)-3,5-difluoropyridin-2-yl)propane-1-sulfonamide.

In a further embodiment are compounds selected from the Examples and Tables, infra.

In another embodiment, with reference to compounds of Formula I, are compounds of Formula Ib:

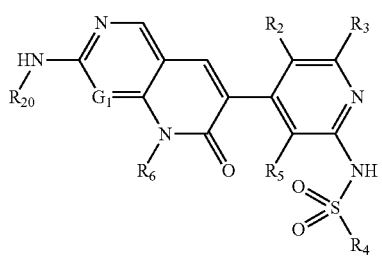

in which:

$G_1$ is selected from N or $CR_8$; $R_8$ is selected from hydrogen, cyano, halo and $C_{1-4}$alkyl optionally substituted by 1 to 3 groups independently selected from hydroxy, halo, oxo, cyano, $C_{1-4}$alkyl, halo-substituted-$C_{1-4}$alkyl, $C_{1-4}$alkoxy, halo-substituted-$C_{1-4}$alkoxy and NHC(O)OR$_9$; wherein $R_9$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

$R_{20}$ is selected from hydrogen and $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, NHC(O)OR$_{10}$ and $S(O)_{0-2}R_{10}$; wherein $R_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

$R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;

$R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;

$R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy; and $R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkoxy.

In another embodiment, $G_1$ is selected from N or CH; $R_{20}$ is selected from methyl and ethyl; wherein said methyl and ethyl are optionally substituted by 1 to 3 groups independently selected from cyano, trifluoromethyl, methoxy-carbonyl-amino, halo and methyl; $R_2$ is fluoro; $R_3$ is hydrogen; $R_4$ is selected from propyl and 3,3,3-trifluoropropyl; $R_5$ is selected from fluoro and chloro; and $R_6$ is methyl.

In another embodiment are compounds selected from: N-(4-(7-(ethylamino)-1-methyl-2-oxo-1,2-dihydro-1,6-naphthyridin-3-yl)-3,5-difluoropyridin-2-yl)propane-1-sulfonamide; N-(3,5-difluoro-4-(8-methyl-2-(methylamino)-7-oxo-7,8-dihydropyrido[2,3-d]pyrimidin-6-yl)pyridin-2-yl)propane-1-sulfonamide; N-(3-fluoro-4-(8-methyl-2-(methylamino)-7-oxo-7,8-dihydropyrido[2,3-d]pyrimidin-6-yl)pyridin-2-yl)propane-1-sulfonamide; (S)-methyl 1-(6-(3,5-difluoro-2-(propylsulfonamido)pyridin-4-yl)-8-methyl-7-oxo-7,8-dihydropyrido[2,3-d]pyrimidin-2-ylamino)propan-2-ylcarbamate; N-(4-(7-(ethylamino)-1-methyl-2-oxo-1,2-dihydro-1,6-naphthyridin-3-yl)-3,5-difluoropyridin-2-yl)propane-1-sulfonamide; N-(3,5-difluoro-4-(8-methyl-2-(methylamino)-7-oxo-7,8-dihydropyrido[2,3-d]pyrimidin-6-yl)pyridin-2-yl)-3,3,3-trifluoropropane-1-sulfonamide; N-(4-(7-(2-cyanoethylamino)-1-methyl-2-oxo-1,2-dihydro-1,6-naphthyridin-3-yl)-3,5-difluoropyridin-2-yl)propane-1-sulfonamide, and N-(5-chloro-4-(7-(ethylamino)-1-methyl-2-oxo-1,2-dihydro-1,6-naphthyridin-3-yl)-3-fluoropyridin-2-yl)propane-1-sulfonamide.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

Pharmacology and Utility

Compounds of the invention modulate the activity of kinases and, as such, are useful for treating diseases or disorders in which kinases contribute to the pathology and/or symptomology of the disease. Examples of kinases that are inhibited by the compounds and compositions described herein and against which the methods described herein are useful include, but are not limited to, B-Raf, including mutant forms of BRaf.

The Ras-Raf-MEK-ERK signaling pathway transmits signals from cell surface receptors to the nucleus and is essential for cell proliferation and survival. Since 10-20% of human cancers harbor oncogenic Ras mutation and many human cancers have activated growth factor receptors, this pathway is an ideal target for intervention.

The Raf family of serine/threonine kinase include three members: C-Raf (or Raf-1), B-Raf and A-Raf. Both the essential role and the position of Raf in many signaling pathways have been demonstrated from studies using deregulated and dominant inhibitory Raf mutants in mammalian cells as well as from studies employing biochemical and genetic techniques to model organisms. In the past, the focus on Raf being an anti-tumor drug target centered on its function as a downstream effector of Ras. However, recent findings suggest that Raf may have a prominent role in the formation of certain tumors with no requirement of an oncogenic Ras allele. In particular, activating alleles of B-Raf have been identified in ~70% of melanomas, 40% of papillary thyroid carcinoma, 30% of ovarian low-grade carcinoma, and 10% of colorectal cancers. Most B-Raf mutations are found within the kinase domain, with a single substitution (V600E) accounting for 80%. The mutated B-Raf proteins activate Raf-MEK-ERK pathway either via elevated kinase activity toward MEK or via activating C-Raf.

Therefore, development of a kinase inhibitor for B-Raf provides a new therapeutic opportunity for treatment of many types of human cancers, especially for metastatic melanomas, solid tumors, brain tumors such as Glioblastoma multiform (GBM), acute myelogenous leukemia (AML), papillary thyroid carcinoma, ovarian low-grade carcinoma, and colorectal cancer. Several Raf kinase inhibitors have been described as exhibiting efficacy in inhibiting tumor cell proliferation in vitro and/or in vivo assays (see, for example, U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, for example, U.S. Pat. Nos. 6,268,391, 6,204, 467, 6,756,410, and 6,281,193; and abandoned U.S. Patent Application Nos. 20020137774 and 20010006975), or for treating breast cancer (see, for example, U.S. Pat. Nos. 6,358, 932, 5,717,100, 6,458,813, 6,268,391, 6,204,467 and 6,911, 446).

The compounds of the present invention inhibit cellular processes involving B-Raf kinase by blocking the signal cascade in these cancer cells and ultimately inducing stasis and/or death of the cells.

In accordance with the foregoing, the present invention further provides a method for preventing or treating lung carcinoma, pancreatic carcinoma, bladder carcinoma, colon carcinoma, myeloid disorders, prostate cancer, thyroid cancer, melanoma, adenomas and carcinomas of the ovary, eye, liver, biliary tract, and nervous system. Further, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 30 mg/kg per body weight. An indicated daily dosage in the larger mammal, e.g. humans, is in the range from about 0.5 mg to about 2000 mg, conveniently administered, e.g. in divided doses up to four times a day or in retard form. Suitable unit dosage forms for oral administration comprise from ca. 1 to 500 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other anti-tumor or anti-proliferative agents, for example, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens, an anti-angiogenesis agent, kinase inhibitor, pan kinase inhibitor or growth factor inhibitor.

Compounds of the invention can be administered in therapeutically effective amounts in combination with one or more suitable excipients selected from corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

An embodiment of the invention is a method further comprising administering to the subject an additional therapeutic agent. The additional therapeutic agent comprises an anticancer drug, a pain medication, an antiemetic, an antidepressant or an anti-inflammatory agent. Further, the additional therapeutic agent is a different Raf kinase inhibitor or an inhibitor of MEK, mTOR, HSP90, AKT, PI3K, CDK9, PAK, Protein Kinase C, a MAP kinase, a MAPK Kinase, or ERK and is administered to the subject concurrently with a compound of the invention.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula Ia can be prepared by proceeding as in the following Reaction Scheme I:

Reaction Scheme I

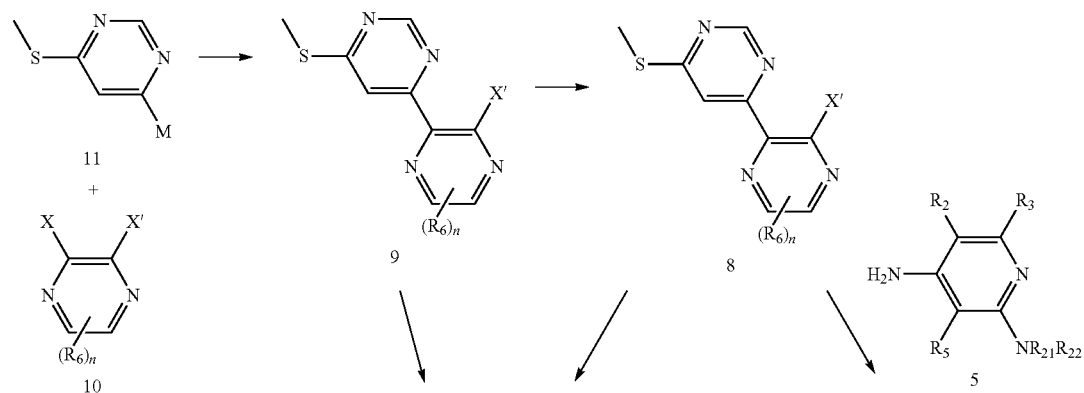

-continued

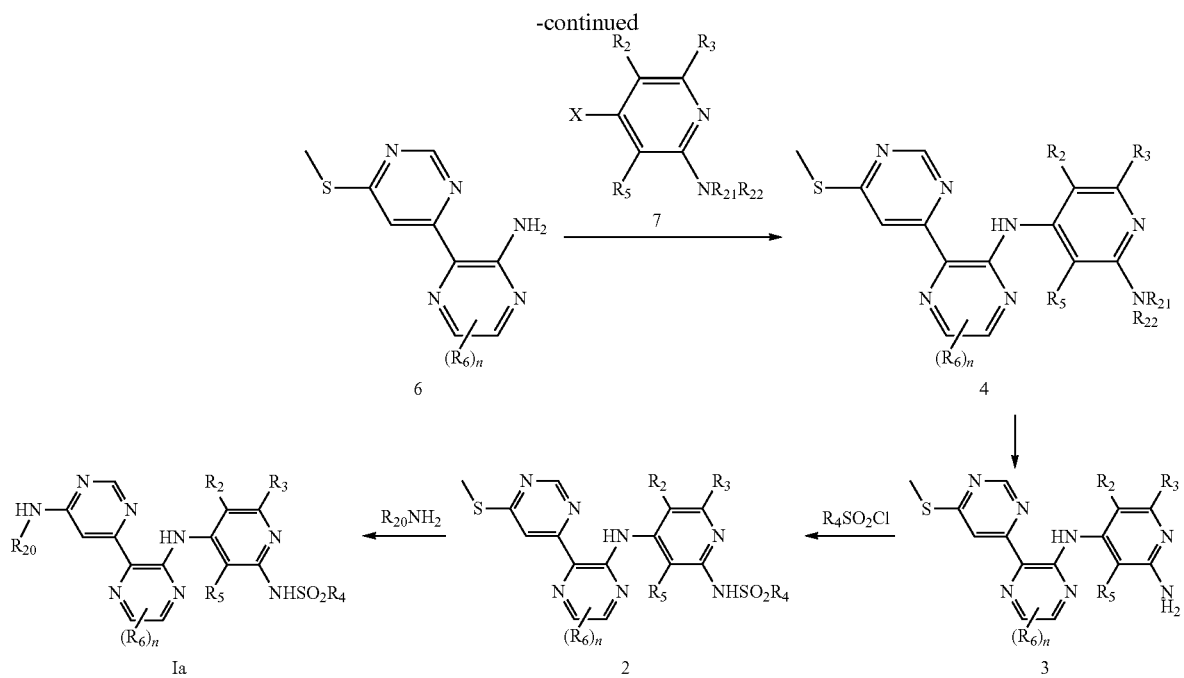

in which X is bromine, chlorine, or iodine; M is a metal selected from the set of tin, boron, and zinc, in each case bearing appropriate ligands; X' is selected from halogen, amino, or a group that can be transformed into halogen or amino; and in which $R_{20}$, $R_2$, $R_3$, $R_4$, $R_5$, and $R_6$ are as defined in the Summary of the Invention. A compound of Formula Ia can be synthesized by reacting a compound of Formula 2 with an amine of formula $R_{20}NH_2$, in a solvent such as isopropanol, DMF, DMSO, or NMP, optionally in the presence of a base such as sodium carbonate or triethylamine, and at a temperature from about room temperature to about 130° C. Prior to reaction with the amine, the sulfide group of a compound of Formula 2 can optionally be oxidized to the corresponding sulfoxide or sulfone, using a suitable oxidizing agent such as m-CPBA in an inert solvent such as dichloromethane, at a temperature from about −78° C. to about room temperature.

Compounds of Formula 2 can, in turn, be prepared by reacting a compound of Formula 3 with a sulfonylating reagent $R_4SO_2Cl$ in the presence of a suitable base (for example, pyridine, triethylamine, 4-(N,N-dimethylamino) pyridine, and the like) and a suitable solvent (such as pyridine, dichloromethane, and the like). The reaction proceeds in a temperature range of about 20° C. to about 100° C. and can take up to about 24 hours to complete. In some instances, the sulfonylating reagent can react twice to produce a bis-sulfonyl derivative. In this instance, the bis-sulfonyl compound can be converted to a compound of Formula 2 by treatment with a suitable base (for example, sodium or potassium carbonate) in the presence of a protic solvent such as methanol or water, optionally in the presence of a cosolvent such as toluene. The reaction takes place in a temperature range of about 20° C. to about 100° C. and can take up to about 24 hours to complete.

Compounds of Formula 3 can be prepared by deprotection of a compound of Formula 4, in which $NR_{21}R_{22}$ represents a protected amino group (for example $R_{21}$ and $R_{22}$ can be BOC and hydrogen, respectively; or both $R_{21}$ and $R_{22}$ can be BOC; or $R_{21}$ and $R_{22}$ can be SEM, and $R_4SO_2$, respectively). In the special case in which $NR_{21}R_{22}$ is equal to $NR_{21}SO_2R_4$, then deprotection of a compound of Formula 4 furnishes a compound of Formula 2 directly.

Compounds of Formula 4 can be prepared by Hartwig/Buchwald reaction of a compound of Formula 5 with a compound of Formula 8, in which X is chlorine, bromine, or iodine, in the presence of a palladium catalyst such as $Pd_2dba_3$ combined with a suitable ligand such as Xantphos, in an inert solvent such as dioxane or toluene, in the presence of a base such as cesium carbonate or sodium t-butoxide, at a temperature of about room temperature to about 140° C.

Compounds of Formula 4 can also be prepared by reaction of a compound of Formula 6 with a compound of Formula 7, in which X is chlorine, bromine, or iodine, and in which $NR_{21}R_{22}$ represents an amino group, a protected amino group, or a sulfonylamino group of formula $NR_{21}SO_2R_4$, and in which $R_{21}$ can be hydrogen or a suitable protecting group. The reaction takes place under similar Hartwig/Buchwald conditions to those described above.

Compounds of Formula 6 can be prepared by reaction of a compound of Formula 8, in which X is fluorine, chlorine, bromine, or iodine, with ammonia, in a solvent such as an alcohol, THF, dioxane, or water, at elevated temperature and pressure. Compounds of Formula 6 can also be prepared from a compound of Formula 9, in which X' is a group that can be converted to $NH_2$; for example, X' can be a protected amino group such as NHBOC.

Compounds of Formula 8 can be prepared from a compound of Formula 9, in which X' is a group that can be converted to X; for example, if X' is $NH_2$, then Sandmeyer reaction conditions can be used, and if X' is an alkoxy group, then treatment with phosphorous oxychloride at elevated temperature, optionally preceded by a separate dealkylation step, can be used.

Compounds of Formula 9 can be prepared by reaction of a compound of Formula 10, in which X is chlorine, bromine, or iodine, and in which X' can be a halogen or a group that can be converted to a halogen, with a compound of Formula 11, in which M is a metal selected from the set of tin, boron, and zinc, in each case bearing appropriate ligands; for example, when M is tin, then the ligated group could be $Bu_3Sn$ or $Me_3Sn$, and when M is zinc then the ligated group can be ZnBr, and when M is boron, then the ligated group can be a boronic acid or boronate ester group. The reaction takes place in the presence of a suitably-ligated palladium catalyst, the exact conditions depending on the particular ligated metal M, and known to those skilled in the art. When X' is chlorine, bromine, or iodine, then reaction of a compound of Formula 10 with a compound of Formula 11 furnishes a compound of Formula 8 directly.

Compounds of Formula Ib in which $R_1$ is $NHR_{20}$ can be prepared by proceeding as in the following Reaction Scheme II:

Reaction Scheme II

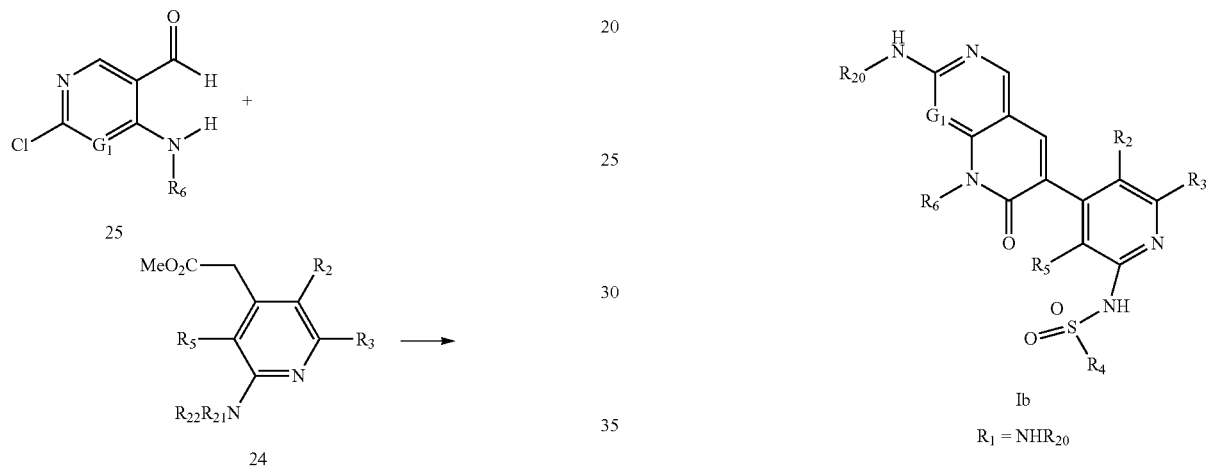

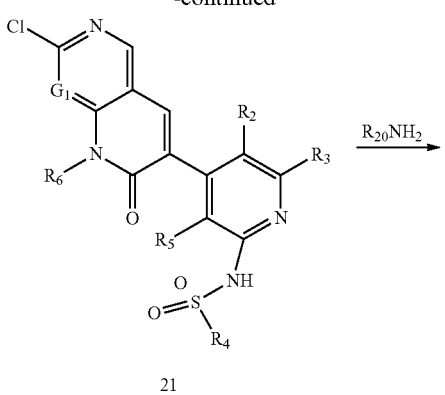

in which $R_{20}$, $R_2$, $R_3$, $R_4$, $R_5$, $R_6$, and $G_1$ are as defined in the Summary of the Invention, and in which $NR_{21}R_{22}$ represents an optionally protected amino group, as described for Reaction Scheme I, following the methods disclosed in WO2005/034869.

Compounds of Formula 25 in which $G_1$ is $CR_8$ can be prepared as in the following Reaction Scheme III:

Reaction Scheme III

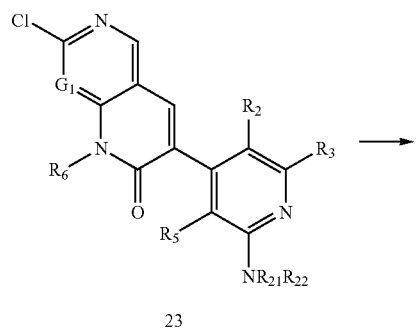

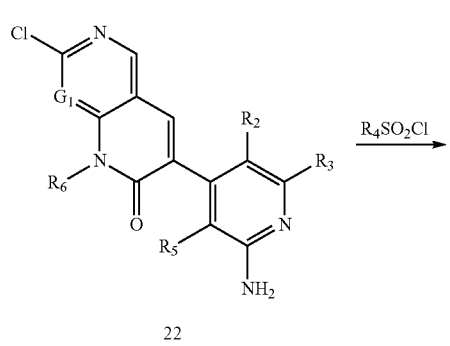

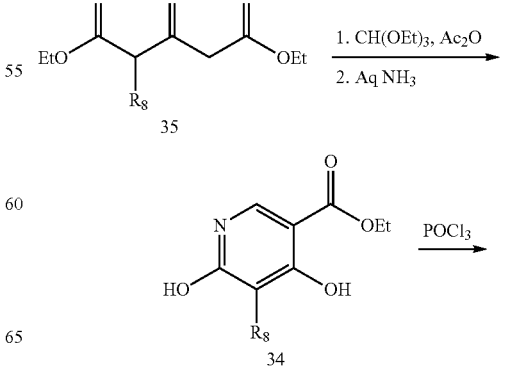

-continued

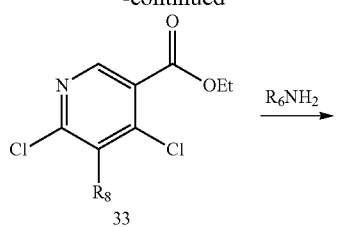
33

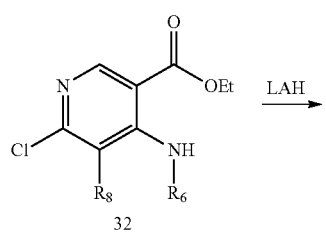
32

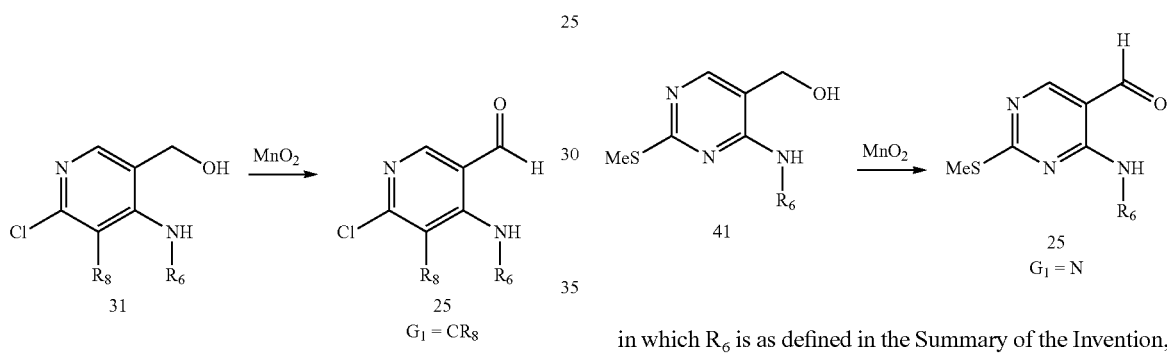
31 → 25 (G₁ = CR₈)

in which R₆ and R₈ are as defined in the Summary of the Invention, following the methods disclosed in WO2005/034869.

Compounds of Formula 25 in which G₁ is N can be prepared as in the following Reaction Scheme IV:

Reaction Scheme IV

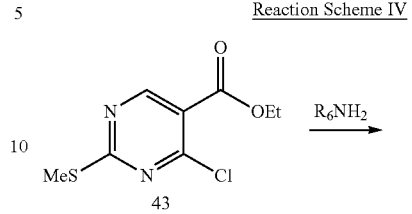
43

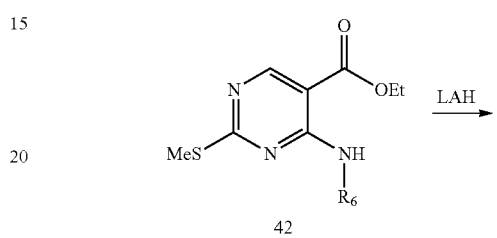
42

41 → 25 (G₁ = N)

in which R₆ is as defined in the Summary of the Invention, following the methods disclosed in J. Med. Chem. 2000, 4006.

Compounds of Formula 24, in which R₂ and R₃ are fluorine, and in which R₂₁ and R₂₂ are hydrogen, can be prepared by multiple routes, following the general methods disclosed in Chem. Eur. J. 2005, 11, 1903-1910 and J. Chem. Soc., Perkin Trans. 1, 2001, 2788-2795, as shown in the following Reaction Scheme V:

Reaction Scheme V

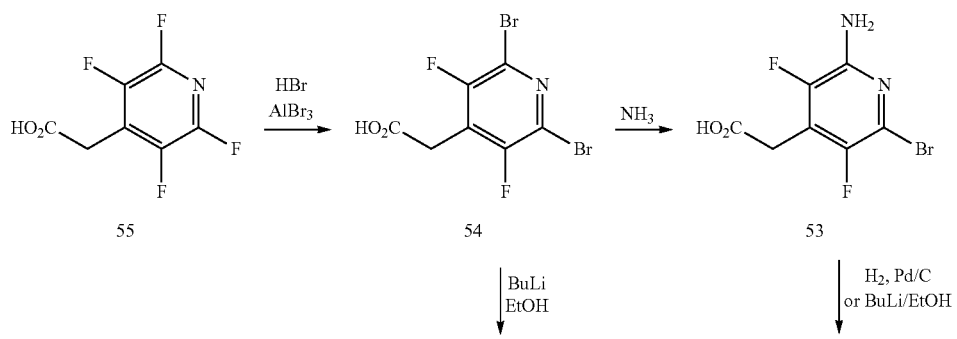
55 → 54 → 53

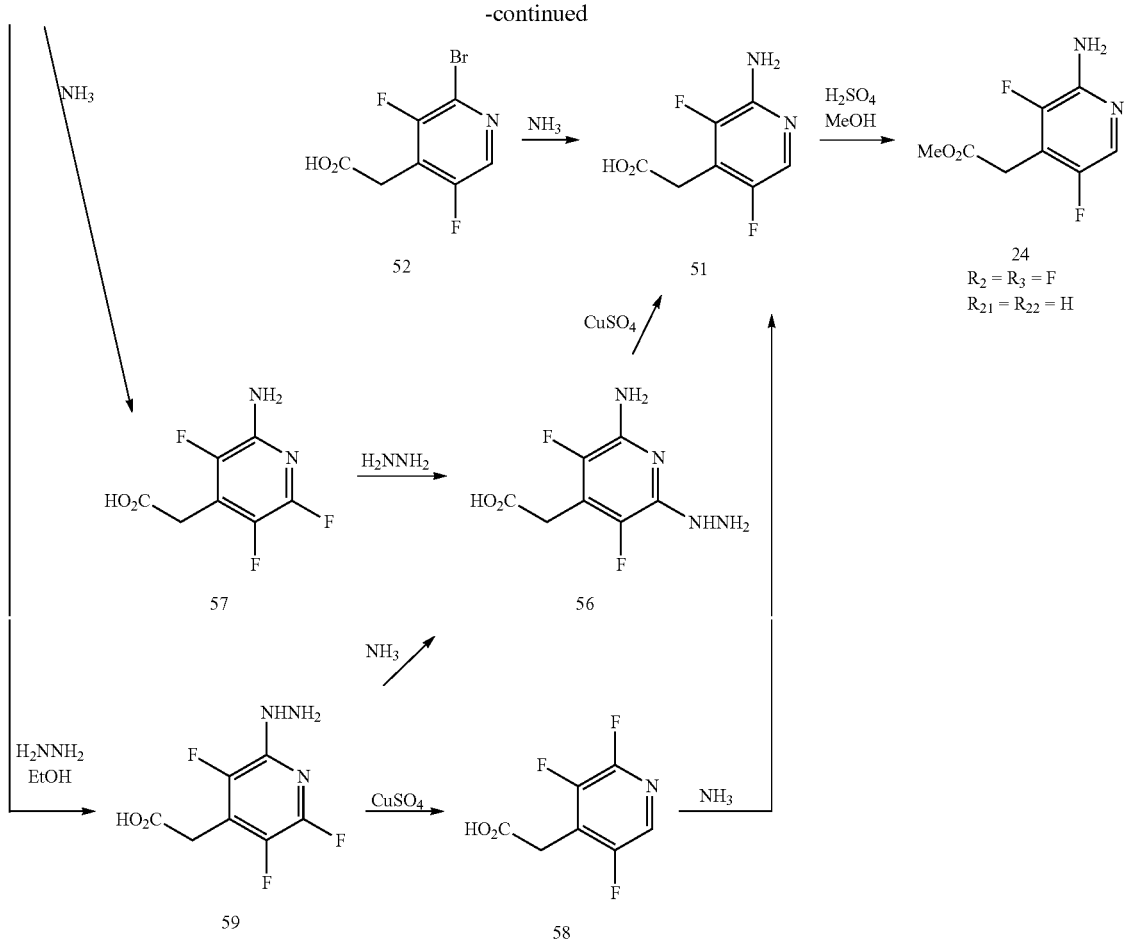
Compounds of Formula Ib in which $R_1$ is $NHR_{20}$ can also be prepared as in the following Reaction Scheme VI:
Reaction Scheme VI
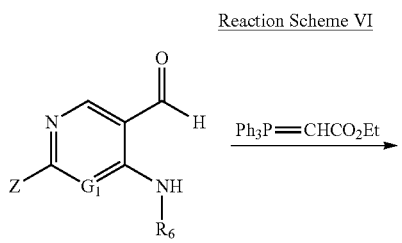
25
66
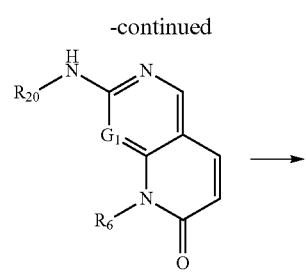
64

-continued

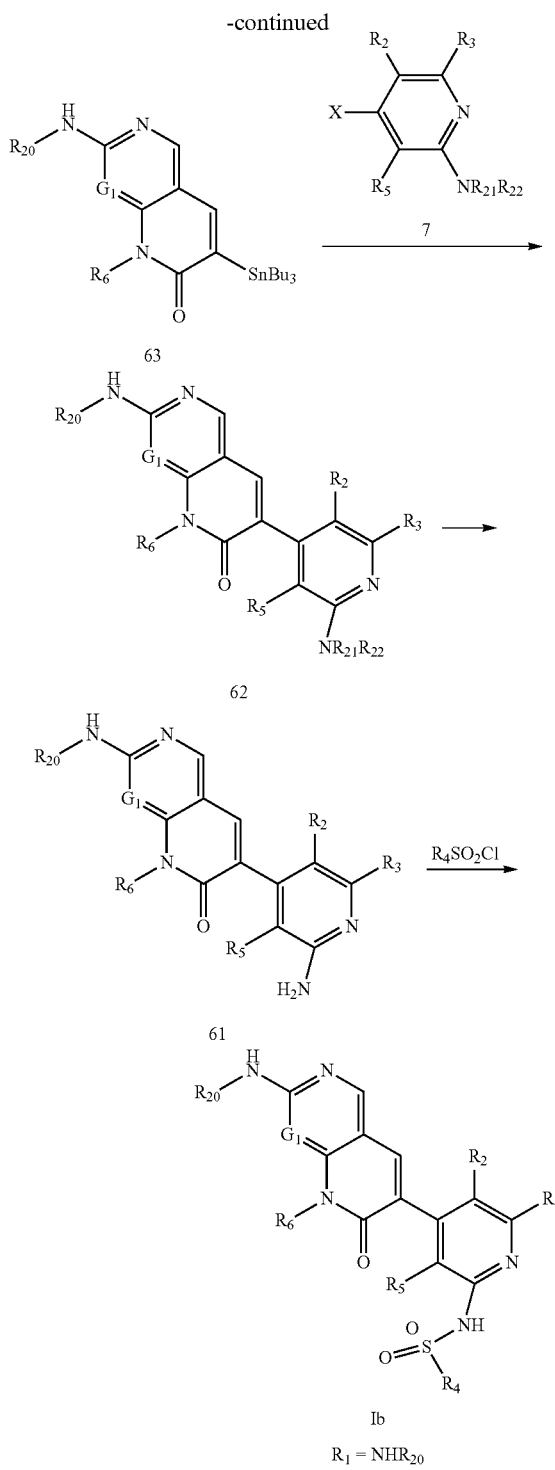

in which $R_2$, $R_3$, $R_4$, $R_5$, $R_6$, $R_{20}$, and $G_1$ are as defined in the Summary of the Invention, and in which $NR_{21}R_{22}$ represents an optionally protected amino group, as described for Reaction Scheme I. When $G_1$ is N, then Z is methylthio; when $G_1$ is $CR_8$, then Z is chloro. Compounds of Formula 1b in which $G_1$ is nitrogen can be prepared using a combination of the methods described in WO2005/034869; J. Med. Chem. 2000, 4606; and Bioorg. Med. Chem. Lett. 2005, 1931.

Compounds of Formula 1b in which $G_1$ is N or $CR_8$ can be prepared by reacting a compound of Formula 61 with a sulfonylating reagent $R_4SO_2Cl$ in the presence of a suitable base (for example, pyridine, triethylamine, 4-(N,N-dimethylamino)pyridine, and the like) and a suitable solvent (such as pyridine, dichloromethane, and the like). The reaction proceeds in a temperature range of about 20° C. to about 100° C. and can take up to about 24 hours to complete. In some instances, the sulfonylating regent can react twice to produce a bis-sulfonyl derivative. In this instance, the bis-sulfonyl compound can be converted to a compound of Formula 61 by treatment with a suitable base (for example, sodium or potassium carbonate) in the presence of a protic solvent such as methanol or water, optionally in the presence of a cosolvent such as toluene. The reaction takes place in a temperature range of about 20° C. to about 100° C. and can take up to about 24 hours to complete.

Compounds of Formula 61 can be prepared by deprotection of a compound of Formula 62, in which $NR_{21}R_{22}$ represents a protected amino group. In the special case in which $NR_{21}R_{22}$ is equal to $NR_{21}SO_2R_4$, then deprotection of a compound of Formula 62 furnishes a compound of Formula Ib directly.

Compounds of Formula 62 can be prepared by Stille reaction of a compound of Formula 63 with a compound of Formula 7, in which X is chlorine, bromine, or iodine, in the presence of a palladium catalyst such as $Pd_2dba_3$ combined with a suitable ligand such as triphenylarsine, with an additive such as copper(I) iodide, in an inert solvent such as DMF, at a temperature of about room temperature to about 100° C., for a time of about 24 to about 72 hours.

Compounds of Formula 63 can in turn be prepared by reacting a compound of Formula 64, in which X is chlorine, bromine, or iodine, with hexabutyldistannane, in the presence of a suitable palladium catalyst such as $Pd(Ph_3P)_4$, in an inert solvent such as THF, at a temperature of about 60 to about 100° C.

Compounds of Formula 64 can be prepared by reaction of a compound of Formula 65 with a suitable brominating agent. Suitable bromination conditions include reaction with phenyl selenium bromide in the presence of pyridine, in an inert solvent such as dichloromethane, at a temperature of about room temperature to about 50° C., or reaction with bromine at a temperature of about −78° C. to about room temperature.

Compounds of Formula 65 can be prepared by reaction of a compound of Formula 66 with a primary amine $R_{20}NH_2$, in a suitable solvent such as NMP or N,N-dimethyl acetamide, at a temperature of about 50 to about 200° C., optionally with microwave irradiation. In the case in which $G_1$ is N and Z is methylthio, then the methylthio group of a compound of Formula 66 can optionally be oxidized to the corresponding sulfoxide or sulfone prior to reaction with the amine $R_{20}NH_2$. Suitable oxidizing conditions include reaction with mCPBA in DCM at a temperature of about −78° C. to about room temperature, optionally in the presence of a base such as sodium bicarbonate.

Compounds of Formula 66 can be prepared by reaction of a compound of Formula 25 with (carbethoxymethylene)triphenylphosphorane or with a suitable Horner-Emmons reagent such as triethylphosphonoacetate in combination with a suitable base, such as n-butyllithium or sodium hydride.

Compounds of Formula Ib in which $R_1$ is hydrogen or $C_{1-4}$alkyl, wherein any alkyl of $R_1$ is optionally substituted by 1 to 3 groups independently selected from hydrogen, halo, cyano, $C_{1-4}$alkyl, halo-substituted-$C_{1-4}$alkyl, $C_{1-4}$alkoxy and halo-substituted-$C_{1-4}$alkoxy, can be prepared using methods similar to those described in Reaction Schemes II-VI, starting with appropriate substituted pyridine or pyrimidine starting materials.

Detailed examples of the synthesis of a compound of Formula Ia and Ib can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt form, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes supra; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates (reference examples) and examples that illustrate the preparation of compounds of Formula I according to the invention.

Abbreviations used are as follows: Dichloromethane (DCM); N,N-dimethyl acetamide (DMA); N,N-dimethyl formamide (DMF); N,N-dimethyl formamide dimethylacetal (DMF DMA); dimethylsulfoxide (DMSO); high pressure liquid chromatography (HPLC); tetrahydrofuran (THF); thin layer chromatography (TLC); and para-toluenesulfonic acid (pTsOH).

Reference Example 1

N-(4-Amino-3,5-difluoropyridin-2-yl)propane-1-sulfonamide

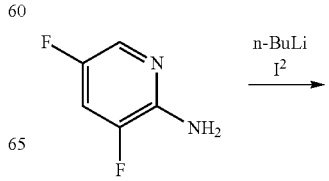

23

-continued

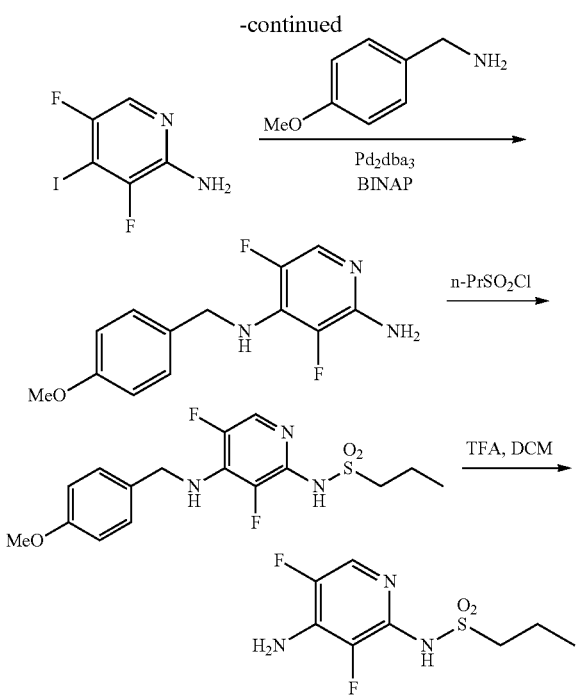

Step 1. 3,5-Difluoro-4-iodopyridin-2-amine n-Butyllithium (41 ml, 1.6 M solution in hexanes, 66 mmol) was added drop wise to a solution of 2-amino-3,5-difluoropyridine (3.4 g, 26 mmol) in THF (100 ml) at −78° C. The mixture was allowed to stir at that temperature for 1.5 hr, then a solution of iodine (20 g, 78 mmol) in THF (30 ml) was added. The mixture was stirred at −78° C. for 15 min, then it was allowed to warm to rt. Saturated aqueous sodium thiosulfate was added, and the mixture was extracted with ethyl acetate. The combined organic layers were dried over sodium sulfate, filtered, and concentrated. The residue was purified by silica gel chromatography (0-25% ethyl acetate in hexanes eluant) to provide the title compound. MS m/z: 297.9 (M+MeCN+1).

Step 2. 3,5-Difluoro-N⁴-(4-methoxybenzyl)pyridine-2,4-diamine

A stirred mixture of 3,5-Difluoro-4-iodopyridin-2-amine (3.0 g, 11.7 mmol), 4-methoxybenzylamine (1.92 g, 14 mmol), Pd$_2$dba$_3$ (1.07 g, 1.2 mmol), BINAP (1.46 g, 2.3 mmol), sodium t-butoxide (1.46 g, 2.3 mmol), and toluene (600 ml) was heated in a sealed vessel with stirring at 130° C. for 16 h. Aqueous sodium bicarbonate solution was added and the mixture was extracted with ethyl acetate. The combined organic extracts were dried over sodium sulfate, filtered, and concentrated. The residue was chromatographed on silica gel (30% ethyl acetate in hexanes eluant) to provide the title compound.

Step 3. N-(3,5-Difluoro-4-(4-methoxybenzylamidin-2-yl)propane-1-sulfonamide

A solution of 3,5-Difluoro-N⁴-(4-methoxybenzyl)pyridine-2,4-diamine (1.3 g, 4.9 mmol), triethylamine (4.1 ml, 29 mmol), and DCM was treated with n-propanesulfonyl chloride (2.2 ml, 19.6 mmol) at 0° C. The mixture was allowed to

24 warm to rt and stirred for 2 h. More n-propanesulfonyl chloride (1.1 ml, 9.8 mmol) was added. After 1 h, aqueous sodium bicarbonate solution was added, and the mixture was extracted with DCM. The combined organic extracts were dried over sodium sulfate, filtered, and concentrated. The residue was dissolved in acetonitrile (10 mL) and aqueous sodium carbonate solution (2M, 10 ml) was added. The mixture was refluxed for 2 h. The cooled reaction mixture was extracted with ethyl acetate, washed with brine, and concentrated. The residue was chromatographed on silica gel (20-30% ethyl acetate in hexanes eluant) to provide the title compound.

Step 4. N-(4-Amino-3,5-difluoropyridin-2-yl)propane-1-sulfonamide

A solution of N-(3,5-Difluoro-4-(4-methoxybenzylamino) pyridin-2-yl)propane-1-sulfonamide (1.05 g) in DCM (50 ml) and TFA (20 ml) was stirred at rt for 16 h. The mixture was concentrated. The residue was taken up in aqueous sodium bicarbonate solution, and the mixture was extracted with DCM. The combined organic extracts were dried over sodium sulfate, filtered, and concentrated. The residue was chromatographed on silica gel (10-50% ethyl acetate in hexanes eluant) to provide the title compound. MS m/z: 251.9 (M+1).

Reference Example 2

4-(3-Chloro-pyrazin-2-yl)-6-methylsulfanyl-pyrimidine

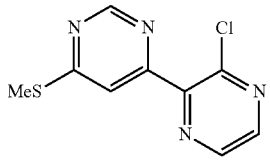 [SMILES: CSc1cc(-c2nccnc2Cl)ncn1]

Step 1. 4-Chloro-6-methylsulfanyl-pyrimidine

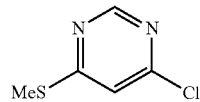

A mixture of 4,6-dichloro-pyrimidine (20.93 g, 140 mmol) and sodium thiomethoxide (10.3 g, 147 mmol) in THF (100 mL) was stirred at room temperature for 16 h, then the reaction mixture was concentrated. The residue was partitioned between ethyl acetate and brine. The organic layer was separated and washed with brine, then dried over sodium sulfate and concentrated. The crude product residue was purified by recrystallization from hexanes (60 mL) to afford the title compound. The mother liquor was concentrated and the residue was purified by silica gel flash chromatography (0% to 10% ethyl acetate in hexanes as eluant) to afford additional title compound containing a small amount of byproduct 4,6- bis methylthio-pyrimidine. ¹H NMR 400 MHz (CDCl₃) δ 8.72 (s, 1H), 7.21 (s, 1H), 2.58 (s, 3H).

Step 2. 4-Iodo-6-methylsulfanyl-pyrimidine

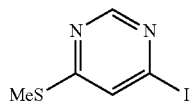

A mixture of 4-chloro-6-methylsulfanyl-pyrimidine (0.54 g, 3.4 mmol), 57% hydriodic acid solution (2.50 mL, 19.0 mmol) and DCM (3 mL) was stirred at room temperature. After 5 h, the resultant solid was collected by filtration and washed with DCM. The cake was dissolved in water (10 mL) and basified with saturated aqueous sodium bicarbonate solution to pH=8. The aqueous layer was extracted with DCM (2×50 mL). The combined organic extracts were washed with brine, dried over sodium sulfate, and concentrated to afford the title compound.

Step 3. 4-Methylsulfanyl-6-tributylstannanyl-pyrimidine

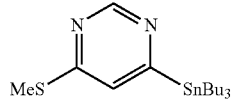

A solution of isopropylmagnesium chloride (2M in THF solution, 5 mL, 10 mmol) was added slowly to a solution of 4-iodo-6-methylsulfanyl-pyrimidine (2.53 g, 10 mol) in THF (50 mL) at −78° C. After 10 min, tri-n-butyltin chloride (2.75 mL, 10 mmol) was added, and the mixture was stirred and allowed to warm to rt overnight. The crude product was purified by silica gel flash chromatography (0 to 10% ethyl acetate in hexanes eluant) to afford the title compound.

Step 4. 4-(3-Chloro-pyrazin-2-yl)-6-methylsulfanyl-pyrimidine

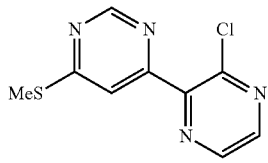 [SMILES: CSc1cc(-c2nccnc2Cl)ncn1]

A mixture of 4-methylsulfanyl-6-tributylstannanyl-pyrimidine (1.80 g, 4.33 mmol), 2,3-dichloro-pyrazine (1.94 g, 13 mmol), triphenylphosphine (0.907 g, 3.46 mmol), palladium (II) acetate (194 mg, 0.866 mmol) and dioxane (15 mL) was degassed and sealed in a pressure tube. After stirring at 120° C. for 16 h, the reaction mixture was concentrated, and the residue purified by silica gel flash chromatography (10% to 30% ethyl acetate in hexanes as eluant) to afford the title compound. ¹H NMR 300 MHz (CDCl₃) δ 9.10 (s, 1H), 8.64 (d, J=2 Hz, 1H), 8.29 (d, J=2 Hz, 1H), 7.70 (s, 1H), 2.64 (s, 3H).

Reference Example 3

N-(3,5-Difluoro-4-iodopyridin-2-yl)-N-((2-(trimethylsilyl)ethoxy)methyl)propane-1-sulfonamide

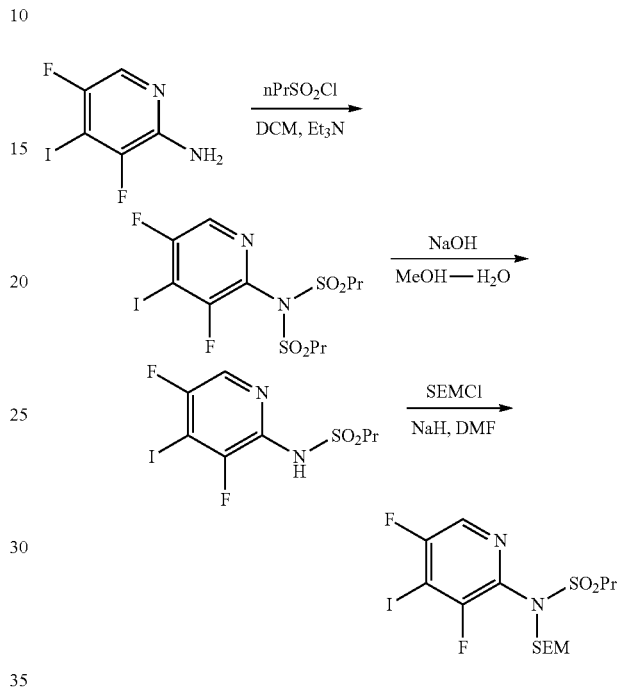

Step 1. N-(3,5-Difluoro-4-iodopyridin-2-yl)-N-(propylsulfonyl)propane-1-sulfonamide To a stirred mixture of 3,5-difluoro-4-iodopyridin-2-amine (200 mg, 0.78 mmol) and triethylamine (240 mg, 2.34 mmol) in DCM (10 ml) at 0° C. was added n-propanesulfonyl chloride (0.28 g, 1.95 mmol). The mixture was allowed to warm to rt and was stirred for 2 h. It was then concentrated to provide the crude product, which was used in the next step without purification. MS m/z 469.1 (M+1).

Step 2. N-(3,5-Difluoro-4-iodopyridin-2-yl)propane-1-sulfonamide

Crude N-(3,5-Difluoro-4-iodopyridin-2-yl)-N-(propylsulfonyl)propane-1-sulfonamide (obtained in Step 1) was stirred with 5% aqueous sodium hydroxide solution (20 ml) at 60° C. for 1 h. The cooled reaction mixture was then acidified with 10% hydrochloric acid to pH<2 and extracted with DCM. The combined extracts were dried over sodium sulfate, filtered, and concentrated. The residue was chromatographed on silica gel (20-30% ethyl acetate in hexanes eluant) to provide the title compound. MS m/z 363.1 (M+1).

Step 3. N-(3,5-Difluoro-4-iodopyridin-2-yl)-N-((2-(trimethylsilyl)ethoxy)-methyl)propane-1-sulfonamide To a solution of N-(3,5-difluoro-4-iodopyridin-2-yl)propane-1-sulfonamide (0.68 g, 1.88 mmol) in anhydrous DMF (25 ml) at 0° C. was added sodium hydride (60% dispersion in mineral oil, 0.15 g, 3.8 mmol). The reaction mixture was stirred for 10 min, and then SEMCl (0.47 g, 2.8 mmol) was added. The mixture was stirred for 1 h and was then concentrated. Water was added and the mixture was extracted with ethyl acetate. The organic layers were combined, dried over sodium sulfate, and concentrated. The residue was chromatographed on silica gel (5 to 20% ethyl acetate in hexanes eluant) to provide the title compound. MS m/z 515.1 (M+Na).

Reference Example 4

N,N-Bis-BOC-3,5-difluoro-4-iodopyridin-2-amin

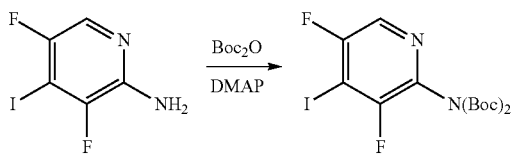

A solution of 3,5-difluoro-4-iodopyridin-2-amine (0.26 g, 1 mmol) and DMAP (18 mg, 0.15 mmol) in DMF (5 mL) was treated with di-t-butyldicarbonate (0.67 g, 3 mmol) at rt. The mixture was stirred at rt for 16 h and was then diluted with water. The mixture was extracted with ethyl acetate, then the combined organic extracts were washed with brine, dried over sodium sulfate, and concentrated. The residue was chromatographed on silica gel (5% ethyl acetate in hexanes eluant) to provide the title compound. MS (m/z) 300.9 (M+1-Boc-t-Bu).

Reference Example 5

6-Chloro-4-(methylamino)nicotinaldehyde

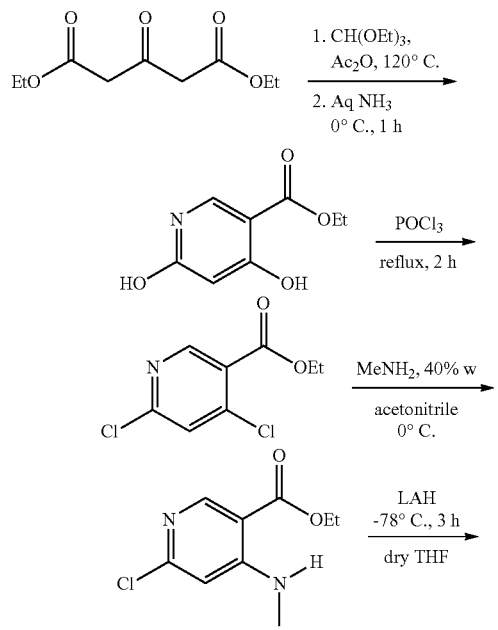

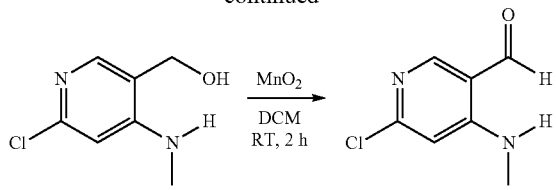

Step 1. Ethyl 4,6-dihydroxynicotinate

Into a 2 L flask was placed diethyl 1,3-acetonedicarboxylate (160 g, 0.79 mol), triethyl orthoformate (129 g, 0.87 mol), and acetic anhydride (161 g, 1.58 mol). The resulting mixture was heated at 120° C. for 1.5 h. The mixture was cooled to rt and volatiles were removed under vacuum. The residue was then cooled in an ice bath and 30% aqueous ammonia (65 mL) was added. The reaction mixture was stirred at 0° C. for 1 h and was then acidified with 2N hydrochloric acid to pH<5. The mixture was concentrated in vacuo. The crude residue was purified by silica gel chromatography (1:1 hexanes/ethyl acetate eluant) to provide the title product.

Step 2. Ethyl 4,6-dichloronicotinate 4,6-Dihydroxynicotinic acid ethyl ester (50 g, 0.3 mol) was mixed with POCl$_3$ (500 mL) in a 2 L flask and heated at 110° C. for 3 h. The reaction mixture was cooled and then concentrated under vacuum. The crude dark-colored residue was poured into ice-water mixture, and the mixture was neutralized with saturated aqueous sodium carbonate solution. The mixture was extracted with ethyl acetate. The combined organic layers were washed with brine, dried over sodium sulfate, filtered, and concentrated. Purification using silica gel chromatography (25% ethyl acetate in hexanes eluant) afforded the title compound as a white solid. $^1$H NMR (300 MHz, CDCl$_3$) δ 8.85 (s, 1H), 7.47 (s, 1H), 4.43 (q, J=7.2 Hz, 2H), 1.41 (t, J=7.2 Hz, 3H).

Step 3. Ethyl 6-chloro-4-(methylamino)nicotinate 4,6-Dichloronicotinic acid ethyl ester (43 g, 195 mmol) was dissolved in acetonitrile (600 mL), and cooled to 0° C., and then methylamine (125 mL of a 40% water solution, 977 mmol) was slowly added. The reaction mixture was stirred at 0° C. for 30 minutes and then allowed to warm to rt over 3 h. Solvent was removed in vacuo and the crude product was purified using silica gel chromatography (1:1 hexanes/ethyl acetate eluant). The title compound was isolated as a white solid. $^1$H NMR (300 MHz, CDCl$_3$) δ 8.66 (s, 1H), 8.12 (bs, 1H), 6.53 (s, 1H), 4.34 (q, J=7.2 Hz, 2H), 2.92 (s, 3H), 1.37 (t, J=7.2 Hz, 3H).

Step 4.
(6-Chloro-4-(methylamino)pyridin-3-yl)methanol

6-Chloro-4-methylaminonicotinic acid ethyl ester (33 g, 156 mmol) was dissolved in anhydrous THF (500 mL) and cooled to −78° C. To the solution was slowly added a solution of LAH (12.5 g, 330 mmol) in THF (500 mL). After the addition was complete, the reaction was kept at −78° C. for 1 h. The mixture was warmed to rt and a small amount of MeOH/ethyl acetate (1/1) was slowly added to destroy the excess LAH. The crude reaction mixture was filtered through a celite plug, washing twice with ethyl acetate. The filtrate was concentrated, and the crude residue was purified by silica gel chromatography (1:1 hexanes/ethyl acetate eluant). The title compound was obtained as a white solid. $^1$H NMR (300 MHz, CDCl$_3$) δ 7.36 (s, 1H), 6.48 (s, 1H), 5.55 (bs, 1H), 4.63 (s, 2H), 2.89 (d, J=5.1 Hz, 3H).

Step 5. 6-Chloro-4-(methylamino)nicotinaldehyde (6-Chloro-4-(methylamino)pyridin-3-yl)methanol (20 g, 116 mmol) was dissolved in DCM (250 mL) and MnO$_2$ (100 g, 1.16 mol) was added. The reaction mixture was stirred at rt overnight, then filtered through a celite plug and washed with ethyl acetate. The filtrate was concentrated to obtain the title compound. $^1$H NMR (300 MHz, CDCl$_3$) δ 9.85 (s, 1H), 8.59 (bs, 1H), 8.31 (s, 1H), 6.59 (s, 1H), 2.96 (d, J=5.1 Hz, 3H).

Example 1

N-(4-(3-(6-(Ethylamino)pyrimidin-4-yl)pyrazin-2-ylamino)-3,5-difluoropyridin-2-yl)propane-1-sulfonamide

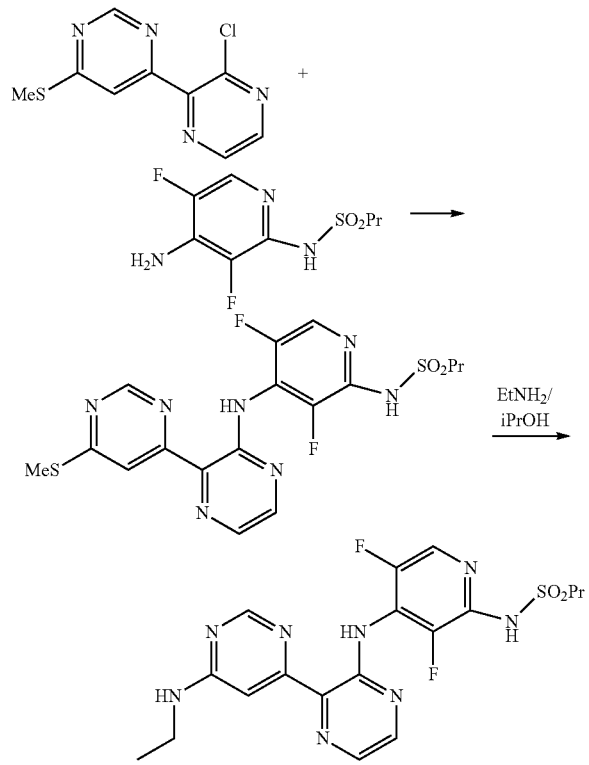

Step 1: N-(3,5-Difluoro-4-(3-(6-(methylthio)pyrimidin-4-yl)pyrazin-2-ylamino)pyridin-2-yl)propane-1-sulfonamide A stirred mixture of 4-(3-chloropyrazin-2-yl)-6-(methylthio)pyrimidine (143 mg, 0.6 mmol), N-(4-amino-3,5-difluoropyridin-2-yl)propane-1-sulfonamide (100 mg, 0.4 mmol), Pd$_2$(dba)$_3$ (109 mg, 0.12 mmol), Xantphos (138 mg, 0.24 mmol), Cs$_2$CO$_3$ (389 mg, 1.19 mmol), 4 Å molecular sieves (500 mg) and dioxane (15 ml) was heated with stirring in a sealed vessel at 150° C. for 5 h. The reaction mixture was cooled to rt and filtered. The filtrate was concentrated, then the residue was chromatographed on silica gel (10-30% ethyl acetate in hexanes eluant) to provide the title compound. MS m/z 454.1 (M+1).

Step 2: N-(4-(3-(6-(Ethylamino)pyrimidin-4-yl)pyrazin-2-ylamino)-3,5-difluoropyridin-2-yl)propane-1-sulfonamide A stirred mixture of N-(3,5-difluoro-4-(3-(6-(methylthio)pyrimidin-4-yl)pyrazin-2-ylamino)pyridin-2-yl)propane-1-sulfonamide (70 mg, 0.15 mmol), ethylamine (70% solution in water, 3 mL) and 2-propanol (3 mL) was heated with stirring at 120° C. for 16 h. The reaction mixture was cooled to rt and concentrated. The residue was chromatographed on silica gel (10-50% ethyl acetate in hexanes eluant) to provide the title compound.

Example 13

N-(4-(7-(Ethylamino)-1-methyl-2-oxo-1,2-dihydro-1,6-naphthyridin-3-yl)-3,5-difluoropyridin-2-yl)propane-1-sulfonamide

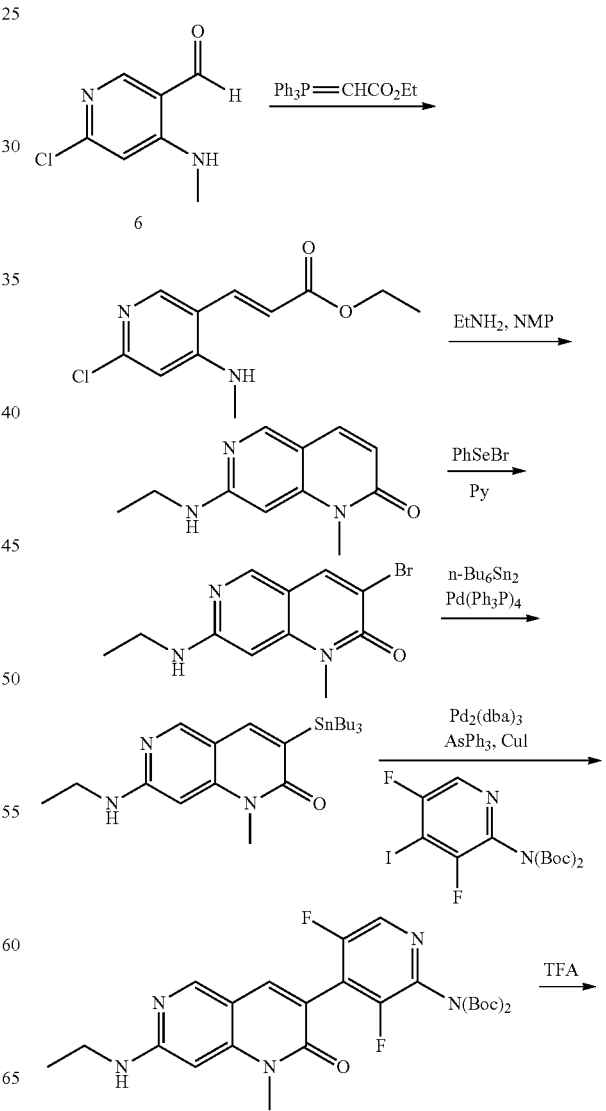

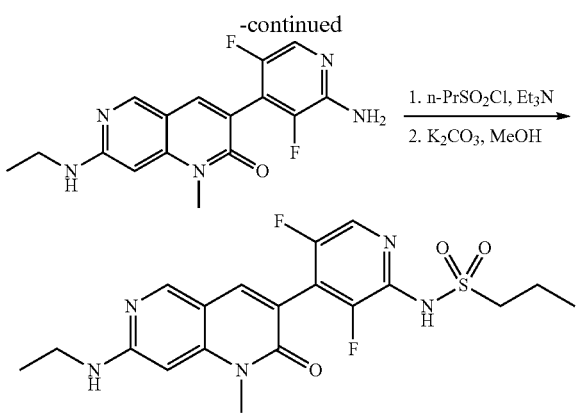

Step 1. (E)-Ethyl 3-(6-chloro-4-(methylamino)pyridin-3-yl)acrylate

To a solution of 6-chloro-4-(methylamino)pyridine-3-carboxaldehyde (3.41 g, 20 mmol) in THF (120 mL) was added (carbethoxymethylene)triphenylphosphorane (8.35 g, 24 mmol). The mixture was heated at reflux for 16 h, and was then cooled and concentrated. The residue was chromatographed on silica gel (12% ethyl acetate in hexanes eluant) to provide the title compound. MS (m/z) 241.0 (M+1).

Step 2. 7-(Ethylamino)-1-methyl-1,6-naphthyridin-2(1H)-one

A vial was charged with (E)-ethyl 3-(6-chloro-4-(methylamino)pyridin-3-yl)acrylate (45 mg), 70% aqueous ethyl amine (1 mL) and NMP (1 mL). The vial was sealed and heated with microwave irradiation for 35 min at 150° C. Aqueous sodium bicarbonate solution was added and the mixture was extracted with dichloromethane. The combined organic extracts were dried over sodium sulfate, filtered, and concentrated. The residue was chromatographed on silica gel (50% ethyl acetate in hexanes eluant) to provide the title compound. MS (m/z) 204.0 (M+1).

Step 3. 3-Bromo-7-(ethylamino)-1-methyl-1,6-naphthyridin-2(1H)-one

To a solution of 7-(ethylamino)-1-methyl-1,6-naphthyridin-2(1H)-one (20 mg, 0.1 mmol) and pyridine (27 μL, 0.3 mmol) in DCM (2 mL) was added phenylselenium bromide (72 mg, 0.3 mmol). The mixture was heated at 39° C. for 6 h, and then the solvent was removed under vacuum. The residue was chromatographed on silica gel (30% ethyl acetate in hexanes eluant) to provide the title compound. MS (m/z) 282.0 (M+1).

Step 4. 3-(Tributylstannyl)-7-(ethylamino)-1-methyl-1,6-naphthyridin-2(1H)-one A tube was charged with 3-bromo-7-(ethylamino)-1-methyl-1,6-naphthyridin-2(1H)-one (45 mg, 0.16 mmol) and tetrakis(triphenylphosphine)palladium(0) (55 mg, 0.047 mmol). The tube was degassed and refilled with nitrogen gas. Hexabutylditin (293 mg, 0.48 mmol) and THF (10 mL) were then added, the tube was sealed, and the mixture was then heated at 80 to 90° C. for 48 h. The mixture was concentrated, and the residue was chromatographed on silica gel (30% ethyl acetate in hexanes eluant) to provide the title compound. MS (m/z) 490.1 (M+1).

Step 5. 3-(2-(N,N-Bis-(t-butoxycarbonyl)amino)-3,5-difluoropyridin-4-yl)-7-(ethylamino)-1-methyl-1,6-naphthyridin-2(1H)-one A tube was charged 3-(tributylstannyl)-7-(ethylamino)-1-methyl-1,6-naphthyridin-2(1H)-one (48 mg, 0.1 mmol), N,N-bis-BOC-3,5-difluoro-4-iodopyridin-2-amine (54 mg, 0.12 mmol), $Ph_3As$ (25 mg, 0.08 mmol), CuI (7.5 mg, 0.04 mmol) and $Pd_2(dba)_3$ (9 mg, 0.01 mmol). The tube was degassed and refilled with nitrogen gas. DMF (10 mL) was added, and then the tube was sealed and heated at 60° C. for 48 h. Aqueous sodium bicarbonate solution was added, and the mixture was extracted with ethyl acetate. The combined organic layers were washed with water and brine, dried over sodium sulfate, filtered, and concentrated. The residue was chromatographed on silica gel (70% ethyl acetate in hexanes eluant) to provide the title compound. MS (m/z) 533.2 (M+1).

Step 6. 3-(2-Amino-3,5-difluoropyridin-4-yl)-7-(ethylamino)-1-methyl-1,6-naphthyridin-2(1H)-one To a solution of 3-(2-(N,N-bis-(t-butoxycarbonyl)amino)-3,5-difluoropyridin-4-yl)-7-(ethylamino)-1-methyl-1,6-naphthyridin-2(1H)-one (32 mg) in DCM (10 mL) was added trifluoroacetic acid (5 mL). The mixture was stirred at room temperature for 1 h. The solvent was removed and the residue was partitioned between ethyl acetate and aqueous sodium bicarbonate solution. The organic phase was washed with brine and was then dried over sodium sulfate, filtered, and concentrated. The residue was chromatographed on silica gel (3% methanol in dichloromethane eluant) to provide the title compound. MS (m/z) 332.1 (M+1).

Step 7. N-(4-(7-(ethylamino)-1-methyl-2-oxo-1,2-dihydro-1,6-naphthyridin-3-yl)-3,5-difluoropyridin-2-yl)propane-1-sulfonamide A solution 3-(2-Amino-3,5-difluoropyridin-4-yl)-7-(ethylamino)-1-methyl-1,6-naphthyridin-2(1H)-one (15 mg, 0.05 mmol), triethylamine (3 ml), and DCM (10 mL) was treated with n-propanesulfonyl chloride (0.05 ml, 0.4 mmol) at 0° C. The mixture was allowed to warm to rt and was stirred for 16 h. Aqueous sodium bicarbonate solution was added, and the mixture was extracted with ethyl acetate. The combined organic extracts were dried over sodium sulfate, filtered, and concentrated. The residue was dissolved in methanol (10 mL) and potassium carbonate (2 g) was added. The mixture was stirred at room temperature for 2 h. Water was added and the mixture was extracted with ethyl acetate, then the combined organic extracts were washed with brine, dried over sodium sulfate, filtered, and concentrated. The residue was chromatographed on silica gel (2% to 3% methanol in DCM eluant) to provide the title compound.

Using variations of the methods outlined above for Examples 1-2, the following examples in Table 1 can be prepared:

TABLE 1

| Compound Number | Structure | A375 CP IC$_{50}$ (μm) | Physical Data $^1$H NMR and/or MS (m/z) |
|---|---|---|---|
| 1 | 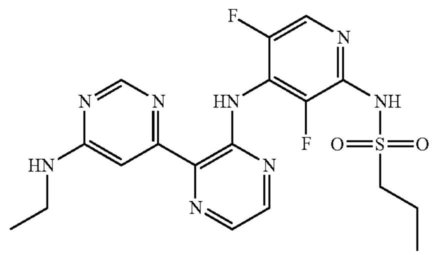 [SMILES: CCCS(=O)(=O)Nc1ncc(F)c(Nc2nccnc2-c2cc(NCC)ncn2)c1F] | 0.013 | MS m/z 451.1 (M + 1); $^1$H NMR 400 MHz (CD$_3$OD) δ 8.56 (s, 1H), 8-19-8.18 (m, 2H), 8.10 (s, 1H), 7.56 (s, 1H), 3.59-3.55 (m, 2H), 3.46-3.44 (m, 2H), 1.95-1.86 (m, 2H), 1.27 (t, J = 7.2 Hz, 3H), 1.09 (t, J = 7.6 Hz, 3H) |
| 2 | 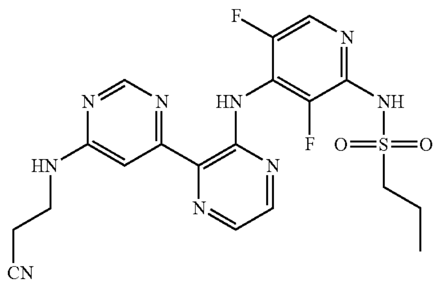 [SMILES: CCCS(=O)(=O)Nc1ncc(F)c(Nc2nccnc2-c2cc(NCCC#N)ncn2)c1F] | 0.003 | MS m/z 476.1 (M + 1); $^1$H NMR 400 MHz (CD$_3$OD) δ 8.56 (s, 1H), 8.11-8.09 (m, 2H), 8.01 (s, 1H), 7.57 (s, 1H), 3.65 (t, J = 6.6 Hz, 2H), 3.49-3.46 (m, 2H), 2.73 (t, J = 6.6 Hz, 2H), 1.83-1.78 (m, 2H), 0.99 (t, J = 7.4, 3H) |
| 3 | 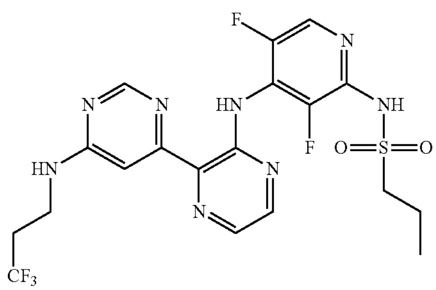 [SMILES: CCCS(=O)(=O)Nc1ncc(F)c(Nc2nccnc2-c2cc(NCCC(F)(F)F)ncn2)c1F] | 0.021 | MS m/z 519.1 (M + 1) |
| 4 | 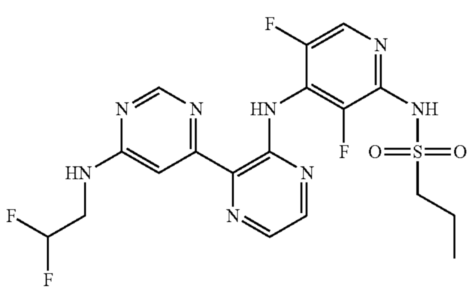 [SMILES: CCCS(=O)(=O)Nc1ncc(F)c(Nc2nccnc2-c2cc(NCC(F)F)ncn2)c1F] | 0.012 | MS m/z 487.1 (M + 1) |
| 5 | 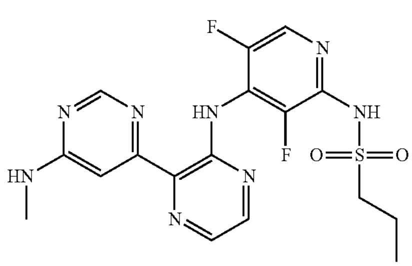 [SMILES: CCCS(=O)(=O)Nc1ncc(F)c(Nc2nccnc2-c2cc(NC)ncn2)c1F] | 0.031 | MS m/z 437.0 (M + 1) |

TABLE 1-continued

| Compound Number | Structure | A375 CP IC$_{50}$ (μm) | Physical Data $^1$H NMR and/or MS (m/z) |
|---|---|---|---|
| 6 | 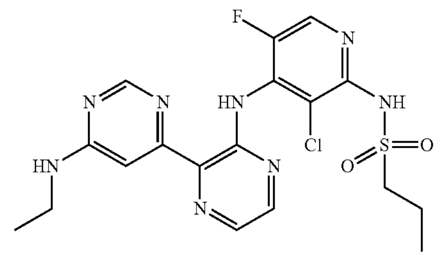 [SMILES: CCCS(=O)(=O)Nc1ncc(F)c(Nc2nccnc2-c2cc(NCC)ncn2)c1Cl] | 0.121 | MS m/z 467.1 (M + 1) |
| 7 | 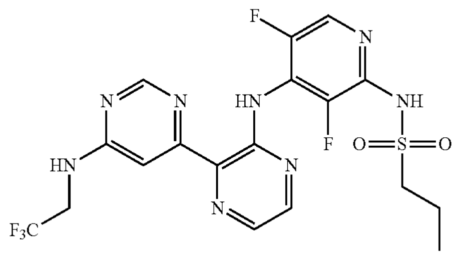 [SMILES: CCCS(=O)(=O)Nc1ncc(F)c(Nc2nccnc2-c2cc(NCC(F)(F)F)ncn2)c1F] | 0.049 | MS m/z 505.1 (M + 1) |
| 8 | 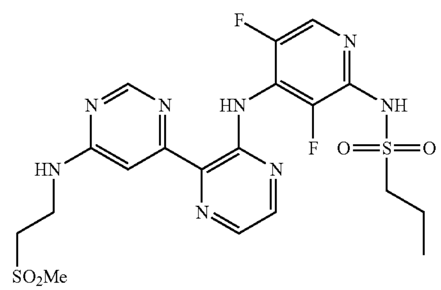 [SMILES: CCCS(=O)(=O)Nc1ncc(F)c(Nc2nccnc2-c2cc(NCCS(C)(=O)=O)ncn2)c1F] | 0.191 | MS m/z 529.1 (M + 1) |
| 9 | 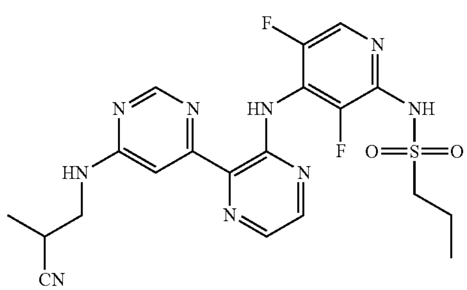 [SMILES: CCCS(=O)(=O)Nc1ncc(F)c(Nc2nccnc2-c2cc(NCC(C)C#N)ncn2)c1F] | | |
| 10 | 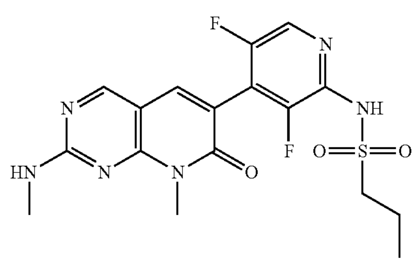 [SMILES: CCCS(=O)(=O)Nc1ncc(F)c(-c2cc3cnc(NC)nc3n(C)c2=O)c1F] | 0.056 | MS m/z 425.1 (M + 1) |

TABLE 1-continued

| Compound Number | Structure | A375 CP IC$_{50}$ (μm) | Physical Data $^1$H NMR and/or MS (m/z) |
|---|---|---|---|
| 11 | 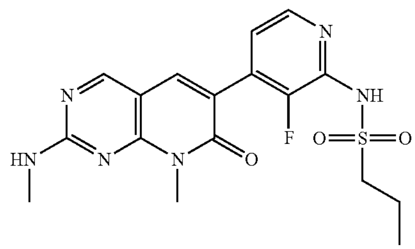 [SMILES: CCCS(=O)(=O)Nc1nccc(-c2cc3cnc(NC)nc3n(C)c2=O)c1F] | 0.229 | MS m/z 407.1 (M + 1) |
| 12 | 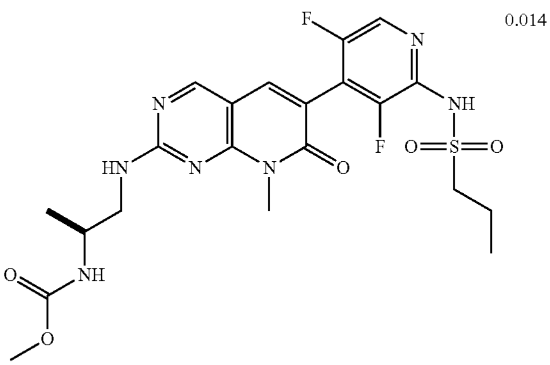 | 0.014 | MS m/z 526.1 (M + 1) |
| 13 | 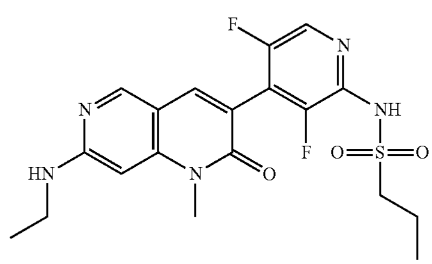 [SMILES: CCCS(=O)(=O)Nc1ncc(F)c(-c2cc3cnc(NCC)cc3n(C)c2=O)c1F] | 0.01 | MS m/z 438.1 (M + 1); $^1$H NMR 400 MHz (CDCl$_3$) δ 8.36 (s, 1H), 8.14 (s, 1H), 7.69 (s, 1H), 6.91 (brs, 1H), 6.01 (s, 1H), 5.04 (t, 1H), 3.64 (s, 3H), 3.50-3.66 (m, 2H), 3.39 (q, 2H), 1.96 (qd, 2H), 1.36 (t, 3H), 1.11 (t, 3H) |
| 14 | 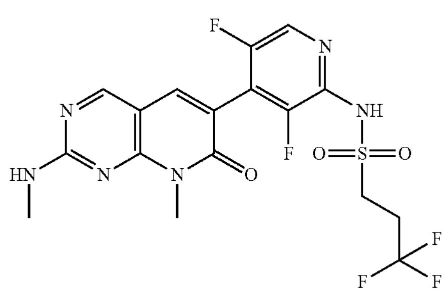 [SMILES: CNc1ncc2cc(-c3c(F)cnc(NS(=O)(=O)CCC(F)(F)F)c3F)c(=O)n(C)c2n1] | 0.13 | MS m/z 479.1 (M + 1) |
| 15 | 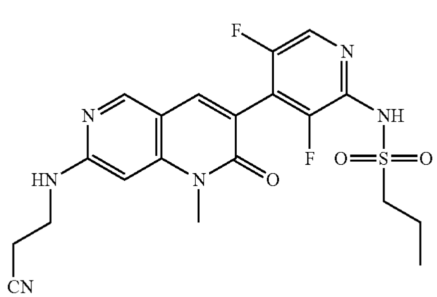 [SMILES: CCCS(=O)(=O)Nc1ncc(F)c(-c2cc3cnc(NCCC#N)cc3n(C)c2=O)c1F] | 0.012 | MS m/z 463.1 (M + 1); $^1$H NMR 400 MHz (CDCl$_3$) δ 8.40 (s, 1H), 8.15 (s, 1H), 7.72 (s, 1H), 6.94 (brs, 1H), 6.20 (s, 1H), 5.24 (t, 1H), 3.84 (q, 2H), 3.69 (s, 3H), 3.60-3.68 (m, 2H), 2.79 (t, 2H), 1.96 (qd, 2H), 1.11 (t, 3H) |

TABLE 1-continued

| Compound Number | Structure | A375 CP IC$_{50}$ (μm) | Physical Data $^1$H NMR and/or MS (m/z) |
|---|---|---|---|
| 16 | 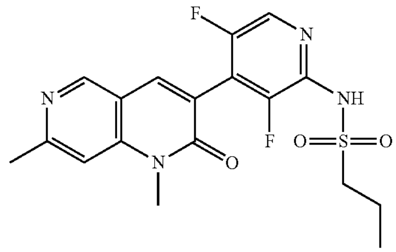 [SMILES: CCCS(=O)(=O)Nc1ncc(F)c(-c2cc3cnc(C)cc3n(C)c2=O)c1F] | | |
| 17 | 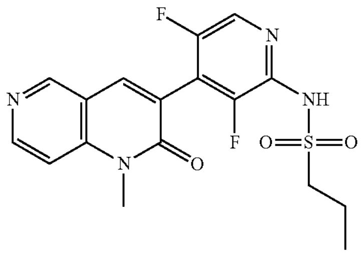 [SMILES: CCCS(=O)(=O)Nc1ncc(F)c(-c2cc3cnccc3n(C)c2=O)c1F] | | |
| 18 | | 0.072 | MS m/z 458.1 (M + 1) |
| 18 | | 0.007 | MS m/z 454.0 (M + 1) |

Example 19

B-Raf V600E/Mek Amplified Luminescence Proximity Homogeneous Assay

B-Raf (V600E; 4 pM) and biotinylated Mek (kinase dead; 10 nM) were combined at 2× final concentrations in assay buffer (50 mM Tris, pH 7.5, 15 mM MgCl$_2$, 0.01% BSA and 1 mM DTT) and dispensed 10 μl per well in assay plates (Greiner white 384 well assay plates #781207) containing 0.5 μl of 40× of a compound of the invention diluted in 100% DMSO. The plate was incubated for 60 minutes at room temperature.

The B-Raf kinase activity reaction was started by the addition of 10 μl per well of 2×ATP (10 μM) diluted in assay buffer. After 3 hours, the reactions were stopped with the addition of 10 μl of stop reagent (60 mM EDTA, 0.01% Tween20). Phosphorylated product was measured using a rabbit anti-p-MEK (Cell Signaling, #9121) antibody and the Alpha Screen IgG (ProteinA) detection Kit (PerkinElmer #6760617R), by the addition of 30 μl to the well of a mixture of the antibody (1:2000 dilution) and detection beads (1:1000 dilution of both beads) in bead buffer (50 mM Tris, pH 7.5, 0.01% Tween20). The additions were carried out under dark conditions to protect the detection beads from light. A lid was placed on top of the plate and the plate was incubated for 1 hour at room temperature. The luminescence was read on a PerkinElmer Envision instrument. The concentration of each compound for 50% inhibition (IC$_{50}$) was calculated by non-linear regression using XL Fit data analysis software.

Compounds of the invention, in free form or in pharmaceutically acceptable salt form, exhibit valuable pharmacological properties, for example, as indicated by the in vitro tests described in this application. For example, compounds of the invention preferably show an IC$_{50}$ in the range of $1 \times 10^{-10}$ to $1 \times 10^{-5}$ M, preferably less than 500 nM, 250 nM, 100 nM and 50 nM for wild type and V600E B-Raf.

Example 20

A375 Cellular Proliferation Assay

A375 is a melanoma cell line that harbors the B-RafV600E mutation. A375-luc cells engineered to express luciferase are plated to 384-well white clear bottom plates as 1,500 cells/50 μl/well in DMEM containing 10% FBS. Compounds of the invention dissolved in 100% DMSO at appropriate concentrations are transferred to the cells by a robotic Pin Tool (100 nl). The cells are incubated for 2 days at 25° C., then 25 μl of BrightGlo™ is added to each well and the plates are read by luminescence. The concentration of each compound for 50% inhibition ($IC_{50}$) was calculated by non-linear regression using XL Fit data analysis software.

Compounds of the invention, in free form or in pharmaceutically acceptable salt form, exhibit valuable pharmacological properties, for example, as indicated by the in vitro tests described in this application. For example, compounds of the invention preferably show an $IC_{50}$ in the range of less than 500 nM, 250 nM, 100 nM, 50 nM and 10 nM in this assay described in example 20.

For example, $IC_{50}$ data for some compounds of the invention in the A375 Cellular Proliferation Assay are shown in the Table, supra.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

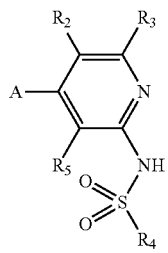

I in which A is selected from a and b:

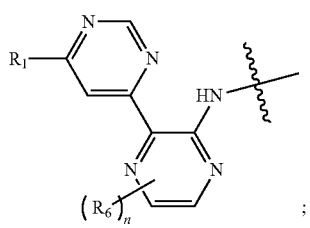

a

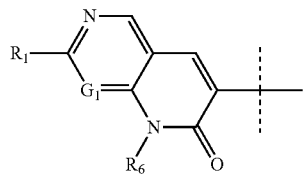

b in which:

$G_1$ is selected from N or $CR_8$; $R_8$ is selected from hydrogen, halo, cyano and $C_{1-4}$alkyl optionally substituted by 1 to 3 groups independently selected from hydroxy, halo, cyano, oxo, $C_{1-4}$alkyl, halo-substituted-$C_{1-4}$alkyl, $C_{1-4}$alkoxy, halo-substituted-$C_{1-4}$alkoxy and NHC(O)$OR_9$; wherein $R_9$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

n is selected from 0, 1 and 2;

$R_1$ is selected from hydrogen, $C_{1-4}$alkyl and —$NHR_{20}$, wherein $R_{20}$ is selected from hydrogen and $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, NHC(O)$OR_{10}$ and $S(O)_{0-2}R_{10}$; wherein $R_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;

$R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;

$R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;

$R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy;

$R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkoxy;

or a pharmaceutically acceptable salt thereof.

2. The compound of claim 1 of Formula Ia:

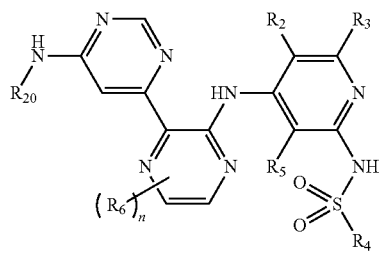

Ia in which:
  n is selected from 0, 1 and 2;
  $R_{20}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, NHC(O)O$R_{10}$ and S(O)$_{0-2}R_{10}$; wherein $R_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;
  $R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;
  $R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;
  $R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy; and
  $R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkyl.

3. The compound of claim 2 in which:
n is 0;
$R_{20}$ is selected from methyl and ethyl; wherein said methyl and ethyl are optionally substituted by 1 to 3 groups independently selected from cyano, trifluoromethyl, methyl-sulfonyl, halo and methyl;
$R_2$ is fluoro;
$R_3$ is hydrogen;
$R_4$ is selected from propyl and 3,3,3-trifluoropropyl; and
$R_5$ is selected from fluoro and chloro.

4. The compound of claim 3 selected from:
N-(4-(3-(6-(ethylamino)pyrimidin-4-yl)pyrazin-2-ylamino)-3,5-difluoropyridin-2-yl)propane-1-sulfonamide;
N-(4-(3-(6-(2-cyanoethylamino)pyrimidin-4-yl)pyrazin-2-ylamino)-3,5-difluoropyridin-2-yl)propane-1-sulfonamide;
N-(3,5-difluoro-4-(3-(6-(3,3,3-trifluoropropylamino)pyrimidin-4-yl)pyrazin-2-ylamino)pyridin-2-yl)propane-1-sulfonamide;
N-(4-(3-(6-(2,2-difluoroethylamino)pyrimidin-4-yl)pyrazin-2-ylamino)-3,5-difluoropyridin-2-yl)propane-1-sulfonamide;
N-(3,5-difluoro-4-(3-(6-(methylamino)pyrimidin-4-yl)pyrazin-2-ylamino)pyridin-2-yl)propane-1-sulfonamide;
N-(3-chloro-4-(3-(6-(ethylamino)pyrimidin-4-yl)pyrazin-2-ylamino)-5-fluoropyridin-2-yl)propane-1-sulfonamide;
N-(3,5-difluoro-4-(3-(6-(2,2,2-trifluoroethylamino)pyrimidin-4-yl)pyrazin-2-ylamino)pyridin-2-yl)propane-1-sulfonamide;
N-(3,5-difluoro-4-(3-(6-(2-(methylsulfonyl)ethylamino)pyrimidin-4-yl)pyrazin-2-ylamino)pyridin-2-yl)propane-1-sulfonamide; and
N-(4-((3-(6-((2-cyanoethyl)amino)pyrimidin-4-yl)pyrazin-2-yl)amino)-3-fluoropyridin-2-yl)propane-1-sulfonamide.

5. The compound of claim 1 of Formula Ib:

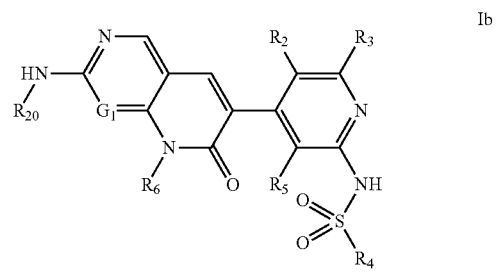

in which:
  $G_1$ is selected from N or C$R_8$; $R_8$ is selected from hydrogen and $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy and NHC(O)O$R_9$; wherein $R_9$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;
  $R_{20}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy, halo-substituted-$C_{1-4}$alkoxy, NHC(O)O$R_{10}$ and S(O)$_{0-2}R_{10}$; wherein $R_{10}$ is $C_{1-4}$alkyl optionally substituted by 1 to 3 groups independently selected from hydroxy, halo, cyano, $C_{1-4}$alkyl, halo-substituted-$C_{1-4}$alkyl, $C_{1-4}$alkoxy and halo-substituted-$C_{1-4}$alkoxy;
  $R_2$ and $R_3$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy;
  $R_4$ is selected from $C_{1-6}$alkyl, $C_{3-8}$cycloalkyl, $C_{3-8}$heterocycloalkyl, $C_{6-10}$aryl and a 5 to 8 member heteroaryl containing 1 to 3 heteroatoms selected from N, O and S; wherein said alkyl, cycloalkyl, heterocycloalkyl, aryl or heteroaryl is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;
  $R_5$ is selected from hydrogen, halo, cyano, $C_{1-4}$alkyl, halo-substituted-$C_{1-4}$alkyl, $C_{1-4}$alkoxy and halo-substituted-$C_{1-4}$alkoxy; and
  $R_6$ is selected from hydrogen and $C_{1-4}$alkyl optionally substituted with a group selected from $C_{6-10}$aryl and $C_{3-8}$cycloalkyl; wherein said alkyl, cycloalkyl or aryl groups of $R_6$ are optionally substituted with 1 to 3 groups independently selected from hydroxy, halo, cyano and $C_{1-4}$alkyl.

6. The compound of claim 5 in which:
$G_1$ is selected from N or CH;
$R_{20}$ is selected from methyl and ethyl; wherein said methyl and ethyl are optionally substituted by 1 to 3 groups independently selected from cyano, trifluoromethyl, methoxy-carbonyl-amino, halo and methyl;
$R_2$ is fluoro;
$R_3$ is hydrogen;

$R_4$ is selected from propyl or ethyl optionally substituted with trifluoromethyl;
$R_5$ is selected from fluoro and chloro; and
$R_6$ is methyl.

7. The compound of claim 6 selected from:
N-(4-(7-(ethylamino)-1-methyl-2-oxo-1,2-dihydro-1,6-naphthyridin-3-yl)-3,5-difluoropyridin-2-yl)propane-1-sulfonamide;
N-(3,5-difluoro-4-(8-methyl-2-(methylamino)-7-oxo-7,8-dihydropyrido[2,3-d]pyrimidin-6-yl)pyridin-2-yl)propane-1-sulfonamide;
N-(3-fluoro-4-(8-methyl-2-(methylamino)-7-oxo-7,8-dihydropyrido[2,3-d]pyrimidin-6-yl)pyridin-2-yl)propane-1-sulfonamide;
(S)-methyl 1-(6-(3,5-difluoro-2-(propylsulfonamido)pyridin-4-yl)-8-methyl-7-oxo-7,8-dihydropyrido[2,3-d]pyrimidin-2-ylamino)propan-2-ylcarbamate;
N-(4-(7-(ethylamino)-1-methyl-2-oxo-1,2-dihydro-1,6-naphthyridin-3-yl)-3,5-difluoropyridin-2-yl)propane-1-sulfonamide;
N-(3,5-difluoro-4-(8-methyl-2-(methylamino)-7-oxo-7,8-dihydropyrido[2,3-d]pyrimidin-6-yl)pyridin-2-yl)-3,3,3-trifluoropropane-1-sulfonamide;
N-(4-(7-(2-cyanoethylamino)-1-methyl-2-oxo-1,2-dihydro-1,6-naphthyridin-3-yl)-3,5-difluoropyridin-2-yl)propane-1-sulfonamide, and
N-(5-chloro-4-(7-(ethylamino)-1-methyl-2-oxo-1,2-dihydro-1,6-naphthyridin-3-yl)-3-fluoropyridin-2-yl)propane-1-sulfonamide.

8. A pharmaceutical composition comprising a compound of claim 1, admixed with at least one pharmaceutically acceptable excipient.

9. The pharmaceutical composition of claim 8, wherein the excipient is selected from the group consisting of corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

10. The pharmaceutical composition of claim 8, further comprising an additional therapeutic agent.

11. The pharmaceutical composition of claim 10, wherein the additional therapeutic agent is selected from an anticancer compound, an analgesic, an antiemetic, an antidepressant, and an anti-inflammatory agent.

* * * * *